(12) United States Patent
Amstoutz et al.

(10) Patent No.: US 9,931,637 B2
(45) Date of Patent: Apr. 3, 2018

(54) SUPPORT APPARATUS FOR A FILTER MEMBRANE AND DISC-SHAPED POROUS SUPPORT MEMBER FOR A FILTER MEMBRANE

(71) Applicant: MERCK PATENT GMBH, Darmstadt (DE)

(72) Inventors: Frederic Amstoutz, Strasbourg (FR); Vincent Schaal, Geispolsheim (FR)

(73) Assignee: MERCK PATENT GMBH, Darmstadt (DE)

( * ) Notice: Subject to any disclaimer, the term of this patent is extended or adjusted under 35 U.S.C. 154(b) by 291 days.

(21) Appl. No.: 14/440,112

(22) PCT Filed: Oct. 16, 2013

(86) PCT No.: PCT/EP2013/003108
§ 371 (c)(1),
(2) Date: May 1, 2015

(87) PCT Pub. No.: WO2014/067621
PCT Pub. Date: May 8, 2014

(65) Prior Publication Data
US 2015/0283516 A1 Oct. 8, 2015

(30) Foreign Application Priority Data
Nov. 2, 2012 (EP) .................................. 12290378

(51) Int. Cl.
*B01L 9/00* (2006.01)
*B01D 69/10* (2006.01)
(Continued)

(52) U.S. Cl.
CPC .............. *B01L 9/52* (2013.01); *B01D 63/087* (2013.01); *B01D 65/00* (2013.01); *B01D 69/10* (2013.01);
(Continued)

(58) Field of Classification Search
CPC .......... B01D 2201/24; B01D 2313/025; B01D 2313/56; B01D 63/087; B01D 65/00;
(Continued)

(56) References Cited

U.S. PATENT DOCUMENTS

| 2,367,794 A | 1/1945 | Marselus |
| 5,112,488 A | 5/1992 | Lemonnier |
| 2006/0273003 A1 | 12/2006 | Sudo |

FOREIGN PATENT DOCUMENTS

| DE | 3711735 C1 | 10/1988 |
| DE | 19823994 A1 | 12/1999 |

(Continued)

OTHER PUBLICATIONS

English translation DE 19823994 A1 (Dec. 1999).*
(Continued)

*Primary Examiner* — John Kim
(74) *Attorney, Agent, or Firm* — Millen, White, Zelano & Branigan, P.C.

(57) ABSTRACT

A support apparatus for a filter membrane comprises a base support and a disc-shaped porous support member. The member is removably received in a seat portion of the base support in fluid communication with a drain. A bottom side of the disc-shaped porous support member is supported in a support plane. The bottom side of the member is unsupported in an area and the unsupported area is adjacent to a space in the seat portion of the base support that is located and dimensioned such that application of a force, onto the top side of the member at a location substantially within the boundaries of the unsupported area at the bottom side will cause the member to pivot/tilt into the space and lift above the support plane at a diagonally opposite side from the location where the force is applied so that it can be easily grasped and removed.

15 Claims, 4 Drawing Sheets

(51) Int. Cl.
    *B01D 65/00*     (2006.01)
    *B01D 63/08*     (2006.01)
    *C12M 1/00*     (2006.01)
    *B01L 3/00*     (2006.01)

(52) U.S. Cl.
CPC ........... *B01L 3/5023* (2013.01); *C12M 47/02* (2013.01); *B01D 2201/24* (2013.01); *B01D 2313/025* (2013.01); *B01D 2313/56* (2013.01); *B01L 2200/025* (2013.01); *B01L 2300/0681* (2013.01); *B01L 2300/0803* (2013.01)

(58) Field of Classification Search
CPC ............... B01D 69/10; B01L 2200/025; B01L 2300/0681; B01L 2300/0803; B01L 3/5023; B01L 9/52; C12M 47/02
See application file for complete search history.

(56) References Cited

FOREIGN PATENT DOCUMENTS

| | | |
|---|---|---|
| DE | 10056354 A1 | 5/2002 |
| EP | 0463897 A1 | 1/1992 |
| JP | 58-61439 B2 | 2/2016 |
| WO | 2005014148 A1 | 2/2005 |

OTHER PUBLICATIONS

International Search Report dated Jan. 30, 2014 issued in corresponding PCT/EP2013/003108 application (pp. 1-3).
Office Action in corresponding Japanese Appln. No. 2015-541027 dated Jun. 23, 2017.
English machine translation of JP05861439B2 to Mitsumi Electric Co Ltd published on Feb. 16, 2016.

* cited by examiner

SUPPORT APPARATUS FOR A FILTER MEMBRANE AND DISC-SHAPED POROUS SUPPORT MEMBER FOR A FILTER MEMBRANE

The present invention concerns the field of biopharmaceutical, hospital, food and beverage industries and specifically relates to a support apparatus for a filter membrane and to a disc-shaped porous support member for a filter membrane to be used in filtration processes in these fields and for filtering liquid samples to effect microbiological analysis.

Various types of single use or reusable apparatus for carrying out sampling and analysis of fluid, preferably liquid samples, for the purpose of filtering such fluids through a filter membrane to recover any microorganisms from the fluid are known. The filter membranes used for these methods most commonly are standard-sized, i.e. 47 mm diameter, circular filter membranes having a defined pore size. A common support apparatus for use with such filter membranes is described in EP-A-0463897. This apparatus is shown in FIG. 1 and comprises a support head 1 with a circular central section 3 and a ring-shaped peripheral section 4 surrounding the central section 3, both supporting a filter membrane 2. The central section 3 of the support is in the form of a removable disc which is made porous and which can be plastic, metal or glass to enable a liquid sample which has passed through the membrane 2 to drain away. The central section 3 is, in the terms and context of the present invention, referred to as the "porous support member for a filter membrane" that is dedicated to support the membrane during filtration operation in the support apparatus. The central support 3 is positioned inside the peripheral support section 4. In the center of the central section 3 and below it, i.e. in fluid communication, a drain 10 is provided to drain through appropriate channels and piping liquid of the liquid sample that has passed the membrane. The support also includes a finger-like plunger 11 with its axis parallel to that of the support and with one end 12 resting on an arm of a lever 14 and its other end positioned flush with the lower surface of the central support section 3 near the circumference of the latter. The plunger can be moved axially to separate the central support section 3 from its seat and from the peripheral support section 4 with a tilting motion by depressing the arm of the lever 14 opposite that on which the end 12 of the plunger 11 rests to cause an axial upward movement of the plunger against a bias force of a spring 17 and effect tilting of the central section 3 and release of the edge of the filter membrane 2. The porous central support section 3 then can be removed from the support apparatus by forceps 18 or by hand.

To secure the test results at a maximum level, it is necessary to decontaminate frequently the filtration support, especially the porous part. The prior art support apparatus is relatively complicated, includes a number of movable parts mechanically linked to each other so that the apparatus overall is difficult to operate, is difficult to decontaminate in view of the many gaps and crevices, requires fluid-tight sealing of the plunger 11 to the environment, for example at 16, and is expensive.

The present invention aims at providing a more simple solution to remove the porous support member from such a support apparatus and to provide a support apparatus that is easier to decontaminate or sterilize and is less costly, yet is more robust to handle.

To solve that problem the present invention provides a support apparatus for a filter membrane as defined in claim 1 and a disc-shaped porous support member for a filter membrane as defined in claim 9. Preferred embodiments of the support apparatus and of the disc-shaped porous support member are defined in the respective dependent claims.

The support apparatus of the present invention for a filter membrane comprises a base support and a disc-shaped porous support member for the filter membrane, wherein the disc-shaped porous support membrane is removably received in a seat portion of the base support in fluid communication with a drain, such that a bottom side of the disc-shaped porous support member is supported in a support plane. According to the invention, the bottom side of the disc-shaped porous support member is unsupported in an area and the unsupported area is adjacent to a space in the seat portion of the base support that is located and dimensioned such that application of a force, preferably of a vertical force or force component directed downward, onto the top side of the disc-shaped porous support member at a location substantially within the boundaries of the unsupported area at the bottom side will cause the disc-shaped porous support member to pivot/tilt into the space and lift up above the support plane at a diagonally opposite side from the location where the force is applied.

According to the invention the structural features for facilitating the pivoting/tilting of the porous support member are formed in the base support. Alternatively, the disc-shaped porous support member of the invention for a filter membrane intended to be removably received in such a seat portion of a base support has a top side for supporting the membrane and a bottom side with one or more support portion(s) defining the support plane. The bottom side is provided with a recess extending from the support plane and extending over an area that is located and dimensioned such that application of a force onto the top side at a location substantially within the boundaries of the recess will cause the disc-shaped porous support member to pivot/tilt and lift up from the support plane.

This disc-shaped porous support member of the invention can be used, for example, in combination with a support apparatus as described above in connection with EP-A-0463897 so that the complicated lifting mechanism including the lever and the plunger can be disposed with. The use of the disc-shaped porous support member of the invention can be advantageous with any support apparatus having a recessed seat portion of a base support because the porous member can be more easily removed without any specific lifting mechanism and without any additional tool or without having to flip over the support apparatus which is also a solution adopted in certain devices according to the prior art.

Therefore, the support apparatus of the invention is easier to clean and maintain and can be manufactured at reduced cost. The porous part can be taken out of its recessed seat by using one hand or a forceps in a very short time. The removal is not dependent on the left-hand or right-hand preference of the user.

The basic idea of the invention is to render the disc-shaped porous support member itself to work like a lever in that a free space is provided either in the seat portion of the base support or at a part of the disc-shaped porous support member itself so that a certain zone of the support member is unsupported. The unsupported zone is located and dimensioned, preferably ring-shaped at an outer periphery of the disc-shaped porous support member, such that application of a force onto the top side substantially in the boundaries of the unsupported area will cause the porous support member to pivot/tilt, thereby diving into the free space in the vicinity of the force application zone and lifting up above the support plane at a substantially diagonal opposite side from that location. In this tilted posture the porous support member can be easily gripped by fingers or forceps and removed from the support apparatus.

The transition from the support plane at the seat portion into the recess can be rounded to guide the tilting movement of the porous support member. Thereby, the tilting movement can be rendered smoother and more controlled.

The top side of the disc-shaped porous support member can be visually and/or structurally marked within the boundaries of the unsupported area to serve as a guidance for the location where the force is to be applied.

The support plane can be defined by a discontinuous seat face including plural spaced-apart seat points or by a substantially continuous seat face. The seat face can be a ring-shaped protrusion between the periphery and the center of the seat face or can comprise a plurality of smaller protrusions arranged within such geometrical area.

The disc-shaped porous support member can be circular, square, triangular, hexagonal or irregularly shaped when seen in a top view.

If the ring-shaped protrusion is used to define the support plane, channels can be provided to extend through the ring-shaped protrusion to provide fluid connection between the outer periphery and a drain that would be located at or in the vicinity of the center of the seat portion.

Such channels can be provided in the seat portion and/or in the disc-shaped porous support member itself at a bottom side.

The invention allows the disc-shaped porous support member to be picked up and removed even from the recessed seat portion of a base support of a support apparatus with the one-hand operation.

In the following various embodiments of the support apparatus and of the disc-shaped porous support member of the invention are described by reference to the attached drawing, in which:

Figure 3:
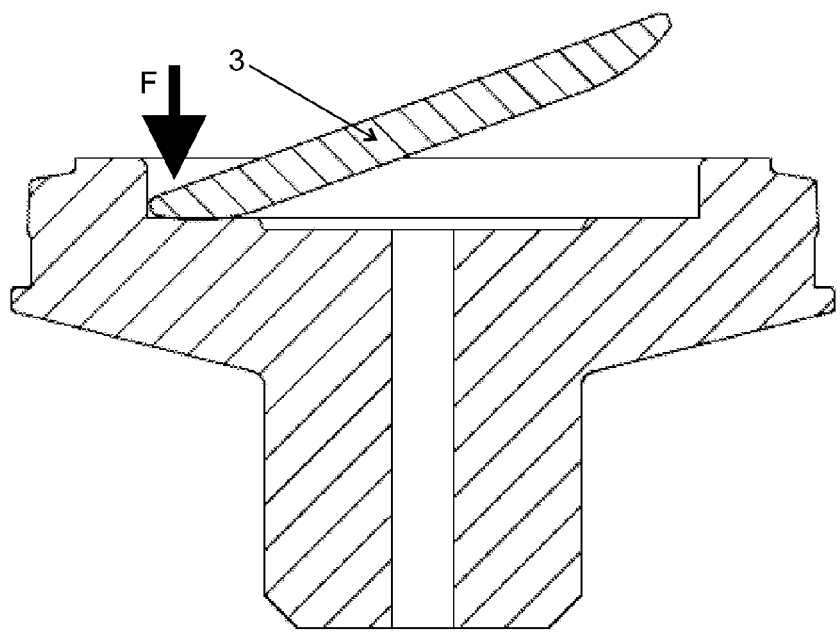
FIG. 3 shows a base support section of a support apparatus with a disc-shaped porous support member of the invention.

The porous support of a support apparatus as shown in FIG. 3 for a filter membrane is essentially one that is known in the art, as for example disclosed and described above in connection with the prior art document EP-A-0463897. The disc-shaped porous support member 3 is, however, prepared in accordance with the invention and it is a circular disc-shaped porous body with a flat top side for supporting the membrane during operation, and a bottom side with one or more support portion(s) defining a support plane.

Figure 1:
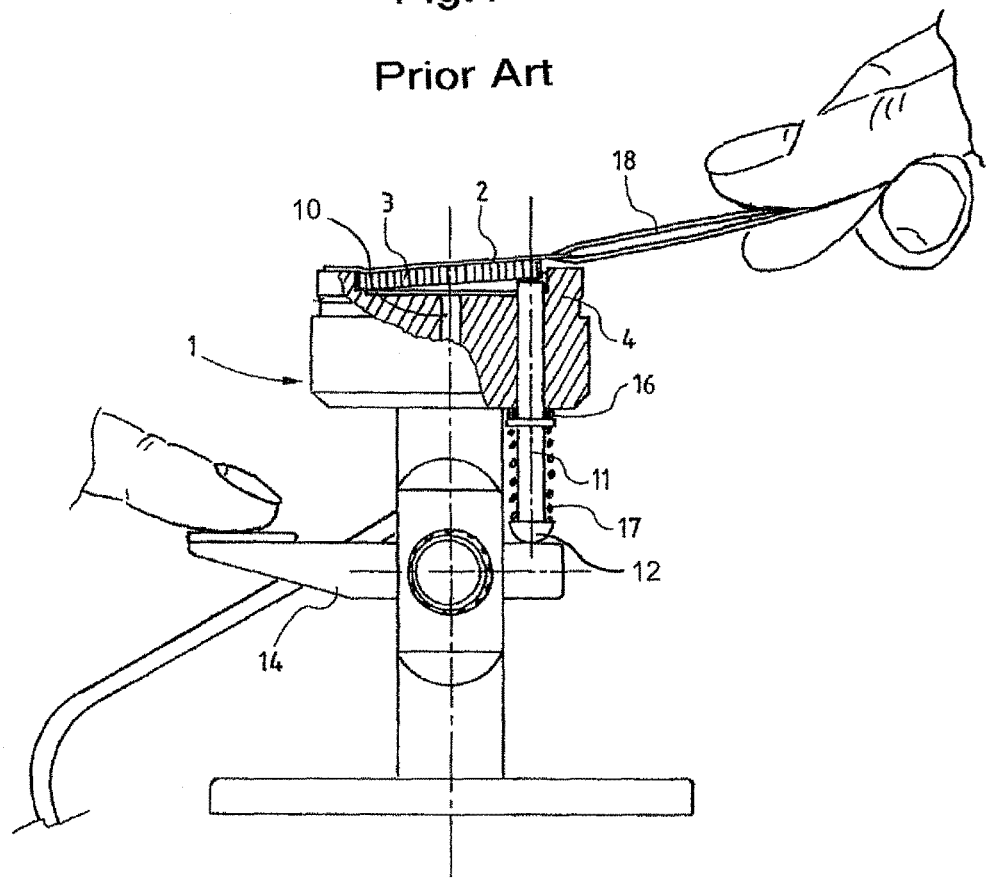
FIG. 1 shows a prior art support apparatus for a filter membrane.
Figure 2:
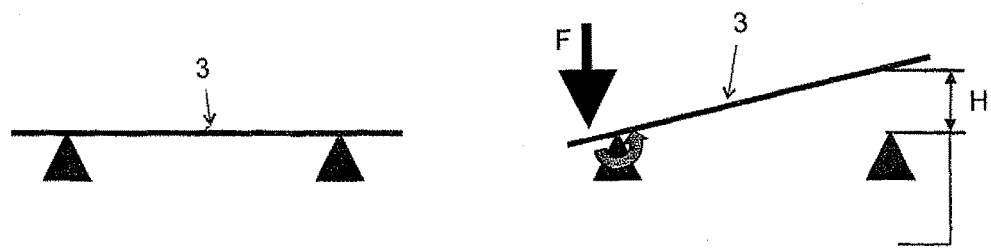
FIG. 2 explains the kinematic concept for tilting the support member according to the present invention.
Figure 4:
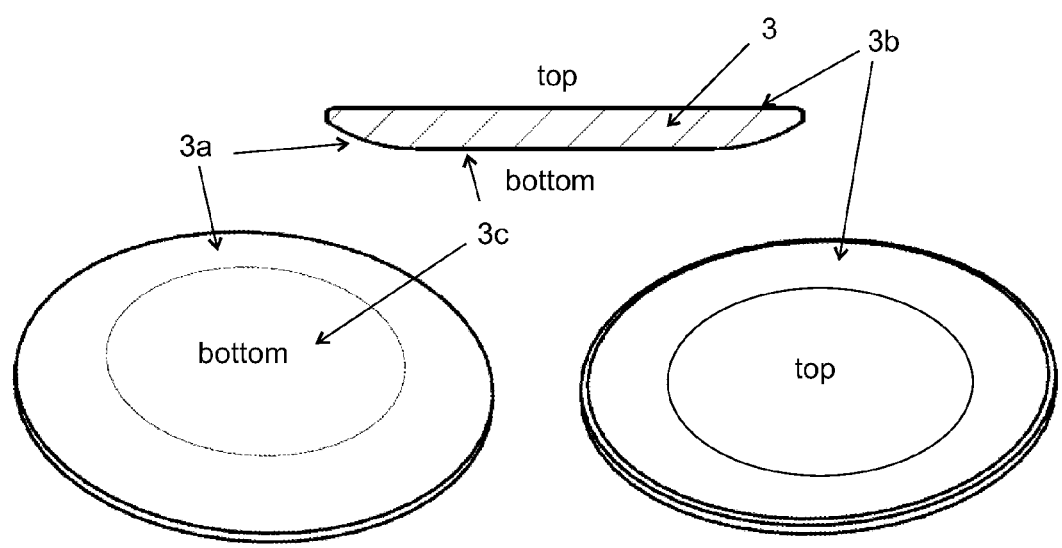
FIG. 4 shows details of the disc-shaped porous support member of FIG. 3.

Deviating from the prior art structure of the disc-shaped porous support members which have a cross-section that is elongated rectangular (as shown for example in FIG. 6), the invention teaches a bottom side to be provided with a recess that is ring-shaped, for example, at the outer periphery of the support member such that one or more support portion(s) 3c are retained. The transition 3a from the support portion(s) at the bottom side, which can be a flat circular surface as shown in FIG. 4 or a further reduced support surface provided a stable support is possible, to the recess is rounded as shown in FIG. 4 to guide the tilting movement of the porous support member when the force F is applied onto the top side at a location 3b substantially within the boundaries of the recess which causes the porous support member to pivot/tilt and lift up from the support plane at an opposite side. Depending on the size and location of the recess, various locations may be suitable for the application of the force. Apparently, the larger the recess and the more outward the location is, the larger the lever arm for tilting the support member and the smaller the required force F. The kinematic concept for lifting/tilting the support member is demonstrated in FIG. 2. Therefore, the unsupported area resulting from the provision of the recess can extend substantially inward from the radial outer periphery towards the center on the bottom side of the support member provided a stable horizontal support posture is possible. Further, the depth of the recess is to be determined depending on the desired lifting height H.

FIG. 4 shows the unsupported area at the bottom side of the porous support member and the corresponding zone for application of the force at the top side in case a ring-shaped recess at the outer peripheral edge portion is chosen.

Figure 5:
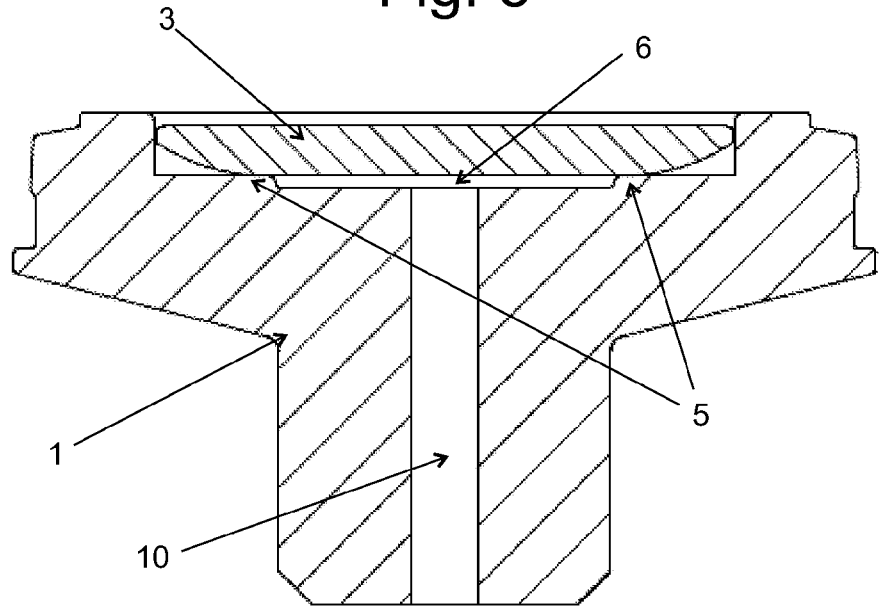
FIG. 5 shows details of an example of the support situation of the disc-shaped porous support member of the invention.

FIG. 5 shows that the actual contact area of the disc in the support plane can be reduced to only a relatively narrow ring-shaped zone 5 if, for example, an additional free volume 6 is provided under the support member 3 communicating with the drain in the base support to facilitate the flow of fluid having passed the filter membrane and disc support in operation. In actual practice, the contact area can be reduced to essentially only three spaced apart points which could still provide a stable horizontal support posture.

Figure 6:
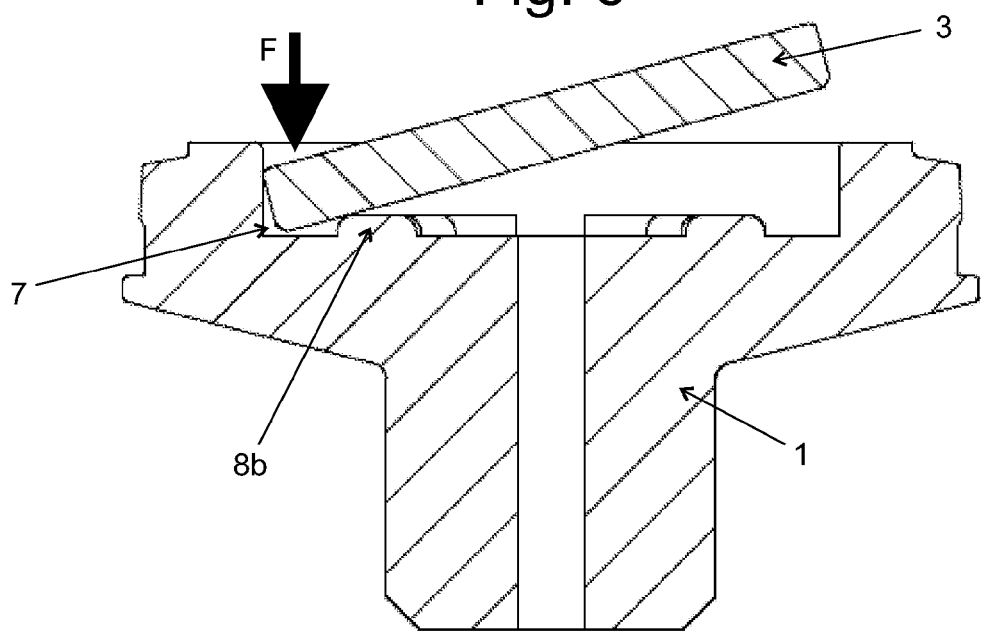
FIG. 6 shows a modified version of the base support of the support apparatus for use in combination with a regular disk-shaped porous support member.
Figure 7:
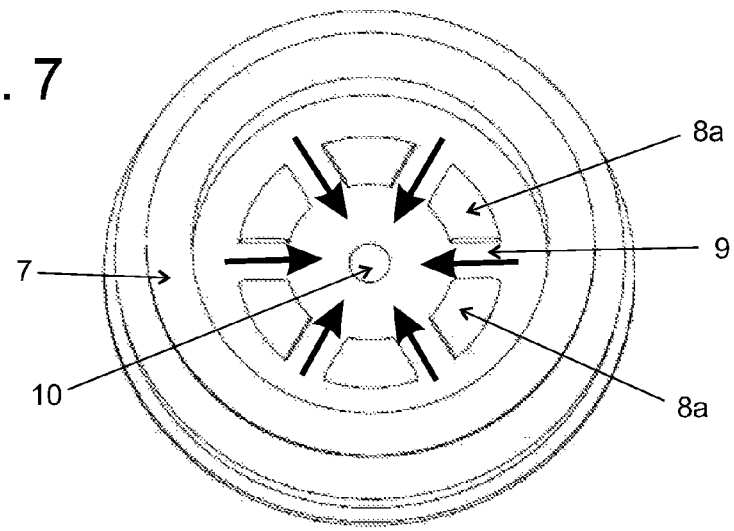
FIG. 7 shows a top view of the seat portion of the base support of a further embodiment of the support apparatus of the invention.

FIG. 6 discloses a modification of the concept of the invention where a common disc-shaped porous support member 3 with a substantially rectangular cross section and without a dedicated tilting recess as described above is used. In this modification, the bottom side of the porous support member is unsupported in an area which is adjacent to a space in the seat portion of the base support that is likewise located and dimensioned such that the application of the force onto the top side of the porous support member, preferably at the outer periphery, at a location substantially within the boundaries of the unsupported area will likewise cause the porous support member to pivot/tilt into the space 7 and lift up above the support plane at the diagonally opposite side from that location. In this embodiment, the support plane is defined by a discontinuous seat face including plural spaced apart seat points or seat portions 8a or by a continuous seat face 8b, which leads to an unsupported area that is ring-shaped at the outer periphery of the disc-shaped porous support member. The seat face may also be located on a ring-shaped protrusion 8b of the seat portion between the outer periphery and the center thereof as shown in FIG. 6. To provide a fluid communication between the outer peripheral recess and the central drain 10 through the ring-shaped protrusion, channels 9 can be provided as shown in FIG. 7. Although not shown in the drawing, the transition from the support plane at the seat portion to the recess in the base support can be rounded as explained in connection with FIG. 4 to guide the tilting movement of the support member into the recess. Then, the pivot point is rather a pivot surface and not a point or line segment as shown in FIG. 6.

Figure 8:
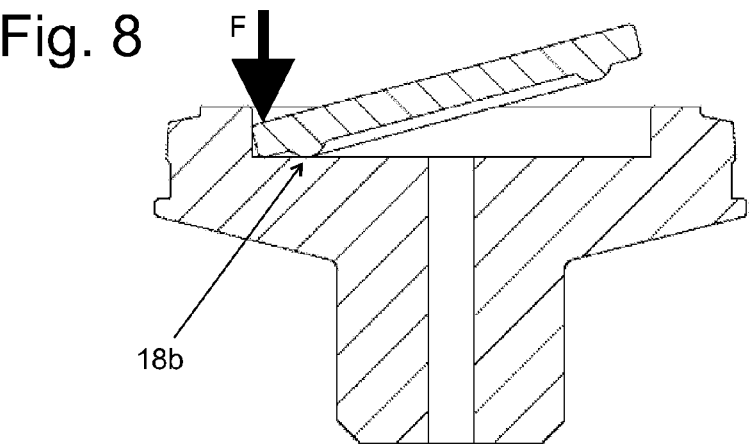
FIG. 8 shows a modified embodiment of a disc-shaped porous support member of the invention.
Figure 9:
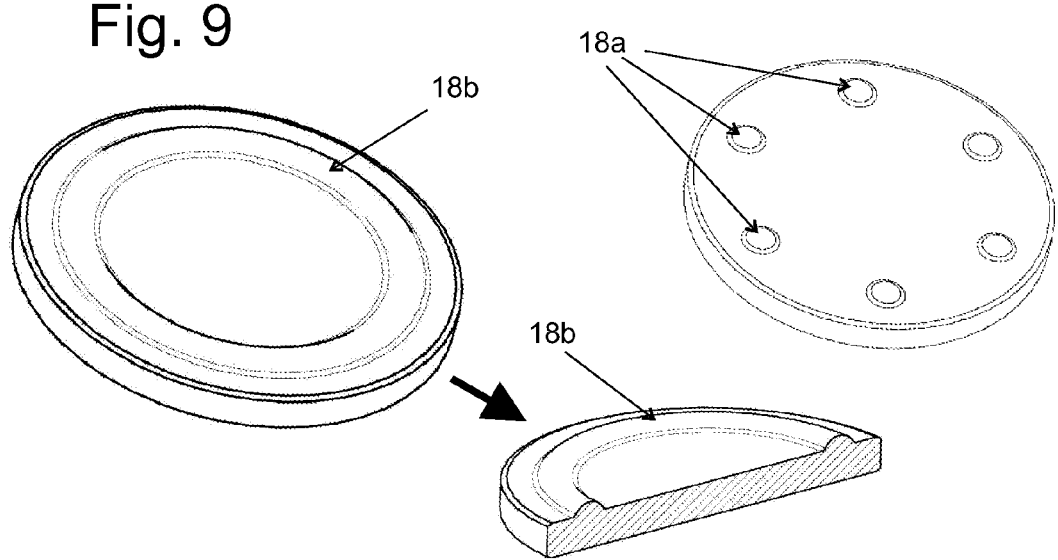
FIG. 9 shows a further modified version of the disc-shaped porous support member of the invention as compared to the support member shown in FIG. 8.

FIGS. 8 and 9 show two alternative embodiments of the disc-shaped porous support member where the recess is ring-shaped at the outer periphery of the support member and is the result of a continuous 18b or discontinuous protrusion 18a within a ring-shaped or circular zone radially spaced from the outer periphery towards the center. In this case a further recess is formed in the more central portion and this recess facilitates the draining of the fluid that has passed the porous member. If the plural, regularly or irregularly spaced apart protrusions 18a are arranged within the ring-shaped or circular zone, as shown in FIG. 9, the communication channels between the outer peripheral recess and the central portion are simultaneously provided.

The invention claimed is:

1. A support apparatus for a filter membrane, comprising a base support and a disc-shaped porous support member for the filter membrane, wherein said disc-shaped porous support member is removably received in a seat portion of said base support in fluid communication with a drain such that a bottom side of the disc-shaped porous support member is supported in a support plane, wherein the bottom side of the disc-shaped porous support member is unsupported in an area and the unsupported area is adjacent to a space in the seat portion of the base support that is located and dimensioned such that application of a force onto the top side of the disc-shaped porous support member at a location within the boundaries of the unsupported area will cause the disc-shaped porous support member to pivot/tilt into the space and lift up above the support plane at a diagonally opposite side from said location.

2. The support apparatus for a filter membrane according to claim 1, wherein the support plane is defined by a discontinuous seat face including plural spaced apart seat points or seat portions or by a continuous seat face.

3. The support apparatus for a filter membrane according to claim 2, wherein the seat face is located on a ring-shaped protrusion of the seat portion between the outer periphery and a center thereof.

4. The support apparatus for a filter membrane according to claim 3, wherein the drain is at or in the vicinity of the center of the seat portion of said base support and channels are provided to extend through the ring-shaped protrusion to provide fluid connection between the outer periphery and the drain.

5. The support apparatus for a filter membrane according to claim 1, wherein the unsupported area is ring shaped at the outer periphery of the disc-shaped porous support member.

6. The support apparatus for a filter membrane according to claim 1, wherein a transition from the support plane at the seat portion to the recess is rounded to guide the tilting movement of the disc-shaped porous support member into the recess.

7. The support apparatus for a filter membrane according claim 1, wherein the disc-shaped porous support member is circular, square, triangle, hexagon or irregularly shaped when seen in a top view.

8. The support apparatus for a filter membrane according to claim 1, wherein the top side of the disc-shaped porous support member and/or the base support is visually and/or structurally marked within the boundaries of the unsupported area to serve as guidance for the location of application of the force.

9. A disc-shaped porous support member for a filter membrane suitable for being removably received in a seat portion of a base support, said disc-shaped porous support member having a top side for supporting the membrane and a bottom side with one or more support portion(s) defining a support plane, wherein
the bottom side is provided with a recess extending from the support plane and extending over an area that is located and dimensioned such that application of a force onto the top side at a location within the boundaries of the recess will cause the disc-shaped porous support member to pivot/tilt and lift up from the support plane.

10. The disc-shaped porous support member according to claim 9, wherein the recess is ring shaped at the outer periphery of the disc-shaped porous support member.

11. The disc-shaped porous support member according to claim 10, wherein the disc-shaped porous support member is circular, square, triangle, hexagon or irregularly shaped when seen in a top view.

12. The disc-shaped porous support member according to claim 10, wherein the top side of the disc-shaped porous support member is visually and/or structurally marked within the boundaries of the recess to serve as guidance for the location of application of the force.

13. The disc-shaped porous support member according to claim 9, wherein the recess is defined between plural protrusions constituting the support portions.

14. The disc-shaped porous support member according to claim 13, wherein the protrusions constituting the support portions are arranged within a ring-shaped or circular zone radially spaced from the outer periphery of the disc-shaped porous support member towards the center.

15. The disc-shaped porous support member according to claim 9, wherein a transition from the support portion(s) at the bottom side to the recess is rounded to guide the tilting movement of the disc-shaped porous support member.

* * * * *